(12) United States Patent
Winkler et al.

(10) Patent No.: US 7,381,178 B2
(45) Date of Patent: *Jun. 3, 2008

(54) TREATMENT OF SPINAL METASTASES

(75) Inventors: Rance A. Winkler, Miramar, FL (US); Timothy J. Patrick, Alpharetta, GA (US); Carribeth B. Ramey, Suwanee, GA (US)

(73) Assignee: Cytyc Corporation, Marlborough, MA (US)

( * ) Notice: Subject to any disclaimer, the term of this patent is extended or adjusted under 35 U.S.C. 154(b) by 240 days.

This patent is subject to a terminal disclaimer.

(21) Appl. No.: 11/260,643

(22) Filed: Oct. 27, 2005

(65) Prior Publication Data

US 2006/0047178 A1 Mar. 2, 2006

Related U.S. Application Data

(63) Continuation of application No. 10/784,083, filed on Feb. 20, 2004, now Pat. No. 6,976,949, which is a continuation of application No. 10/269,555, filed on Oct. 11, 2002, now Pat. No. 6,695,760.

(51) Int. Cl.
 *A61N 5/00* (2006.01)
 *A61F 2/44* (2006.01)
 *A61M 29/00* (2006.01)
(52) U.S. Cl. ............... 600/7; 623/17.16; 606/192
(58) Field of Classification Search ........ 128/897–899; 600/1–8, 425, 427, 471, 476, 160; 604/891.1, 604/96.01, 104, 97.01, 103.5, 915, 921, 171, 604/101.05, 264, 280, 93; 606/61, 94, 192, 606/171, 101.05; 378/64.65; 623/23.62, 623/11.11, 22.11, 18.11, 23.11, 17.16, 17.11, 623/17.15, 1.42, 1.39, 1.45, 16–23; 424/422, 424/423, 426

See application file for complete search history.

(56) References Cited

U.S. PATENT DOCUMENTS 3,324,847 A 6/1967 Zoumboulis (Continued)

FOREIGN PATENT DOCUMENTS

EP 0 340 881 10/1992

(Continued)

OTHER PUBLICATIONS

Ashpole, R.D. et al., "A New Technique of Brachytherapy for Malignant Gliomas with Caesium-137: A New Method Utilizing a Remote Afterloading System," *Clinical Oncology* 2:333-337 (1990).

(Continued)

*Primary Examiner*—John P Lacyk
(74) *Attorney, Agent, or Firm*—Heather Larson; Mark J. Casey (57) ABSTRACT

A radiotherapy system, and preferably a brachytherapy system, for delivering radiation to tissue surrounding an interstitial space is provided. While the system can be used for a variety of purposes, the system is preferably used to treat spinal metastases. In general, the system includes a catheter member having a proximal end, a distal end, and an inner lumen extending therethrough, and a structural support adapted to fit within an interstitial space in load bearing portion of a patient's body and having an internal space for removably receiving the distal end of the catheter member. At least one anchoring element can be disposed proximate to the distal end of the catheter. The anchoring element is preferably adapted to fit within the internal space in the structural support so as to anchor the distal end of the catheter therein. The system further includes a radiation source disposable within the internal space of the structural support through the lumen in the catheter for delivering radiation to tissue surrounding the interstitial space.

15 Claims, 4 Drawing Sheets

U.S. PATENT DOCUMENTS

| | | |
|---|---|---|
| 3,872,856 A | 3/1975 | Clayton |
| 4,417,576 A | 11/1983 | Baran |
| 4,706,652 A | 11/1987 | Horowitz |
| 4,754,745 A | 7/1988 | Horowitz |
| 4,763,642 A | 8/1988 | Horowitz |
| 4,821,725 A | 4/1989 | Azam et al. |
| 4,867,741 A | 9/1989 | Portnoy |
| 5,015,247 A | 5/1991 | Michaelson |
| 5,084,001 A | 1/1992 | Van't Hooft et al. |
| 5,084,015 A | 1/1992 | Moriuchi |
| 5,106,360 A | 4/1992 | Ishiwara et al. |
| 5,112,303 A | 5/1992 | Pudenz et al. |
| 5,152,747 A | 10/1992 | Olivier |
| 5,236,410 A | 8/1993 | Granov et al. |
| 5,422,926 A | 6/1995 | Smith et al. |
| 5,484,384 A | 1/1996 | Fearnot |
| 5,562,594 A | 10/1996 | Weeks |
| 5,566,221 A | 10/1996 | Smith et al. |
| 5,720,717 A | 2/1998 | D'Andrea |
| 5,724,400 A | 3/1998 | Swerdloff et al. |
| 5,741,253 A | 4/1998 | Michaelson |
| 5,800,333 A | 9/1998 | Liprie |
| 5,803,895 A | 9/1998 | Kronholz et al. |
| 5,851,182 A | 12/1998 | Sahadevan |
| 5,863,284 A | 1/1999 | Klein |
| 6,036,631 A | 3/2000 | McGrath et al. |
| 6,120,540 A * | 9/2000 | Apple et al. ............. 623/11.11 |
| 6,413,204 B1 | 7/2002 | Winkler et al. |
| 6,695,760 B1 * | 2/2004 | Winkler et al. ................. 600/7 |
| 6,976,949 B2 * | 12/2005 | Winkler et al. ................. 600/7 |

FOREIGN PATENT DOCUMENTS

| | | |
|---|---|---|
| EP | 0 867 200 | 9/1998 |
| WO | WO-92/10932 | 7/1992 |
| WO | WO-93/09724 | 5/1993 |
| WO | WO-97/19723 | 6/1997 |
| WO | WO-99/11325 A1 | 3/1999 |
| WO | WO-99/33515 A2 | 7/1999 |
| WO | WO-99/42163 A1 | 9/1999 |
| WO | WO-01/43826 A1 | 6/2001 |
| WO | WO-01/68005 A2 | 9/2001 |

OTHER PUBLICATIONS

Ravinder, N. et al., "Development of an[241] Am Applicator for Intracavitary Irradiation of Gynecologic Cancers," *I.J. Radiation Oncology, Biology, Physics* 14:969-978 (1988).

International Search Report, from PCT/US03/32686, issued Apr. 15, 2004.

* cited by examiner

TREATMENT OF SPINAL METASTASES

RELATED APPLICATIONS

This application is a continuation of U.S. patent application Ser. No. 10/784,083, filed on Feb. 20, 2004, now U.S. Pat. No. 6,976,949, which is a continuation of U.S. patent application Ser. No. 10/269,555, filed on Oct. 11, 2002, now U.S. Pat. No. 6,695,760 B1.

FIELD OF THE INVENTION

The invention relates generally to apparatus for use in treating proliferative tissue disorders, and more particularly to an apparatus for the treatment of such disorders in the body by the application of radiation.

BACKGROUND OF THE INVENTION

Malignant tumors are often treated by surgical resection of the tumor to remove as much of the tumor as possible. Infiltration of the tumor cells into normal tissue surrounding the tumor, however, can limit the therapeutic value of surgical resection because the infiltration can be difficult or impossible to treat surgically. Radiation therapy can be used to supplement surgical resection by targeting the residual tumor margin after resection, with the goal of reducing its size or stabilizing it. Radiation therapy, or surgical excision followed by radiation therapy, is commonly used to treat spinal metastases. Metastases are tumors that have grown in a location that is remote from the site that the tumor started, and spinal metastases result from the spread of cancer cells into a patient's vertebral column.

Radiation therapy can be administered through one of several methods, or a combination of methods, including external-beam radiation, stereotactic radiosurgery, and permanent or temporary interstitial brachytherapy. The term "brachytherapy," as used herein, refers to radiation therapy delivered by a spatially confined radioactive material inserted into the body at or near a tumor or other proliferative tissue disease site. Owing to the proximity of the radiation source, brachytherapy offers the advantage of delivering a more localized dose to the target tissue region.

For example, brachytherapy is performed by implanting radiation sources directly into the tissue to be treated. Brachytherapy is most appropriate where 1) malignant tumor regrowth occurs locally, within 2 or 3 cm of the original boundary of the primary tumor site; 2) radiation therapy is a proven treatment for controlling the growth of the malignant tumor; and 3) there is a radiation dose-response relationship for the malignant tumor, but the dose that can be given safely with conventional external beam radiotherapy is limited by the tolerance of normal tissue. In brachytherapy, radiation doses are highest in close proximity to the radiotherapeutic source, providing a high tumor dose while sparing surrounding normal tissue. Interstitial brachytherapy is useful for treating malignant brain and breast tumors, among others.

While devices exist for delivering radiation to treat metastases, there is still a need for 6 instruments which can be used to provide brachytherapy to target tissue within a load bearing portion of a human body, such as within a patient's spine.

SUMMARY OF THE INVENTION

The present invention generally provides a brachytherapy system for treating metastases within a load bearing portion of a patient's body. The system includes a structural support having an internal space and being adapted to fit within an interstitial space within a load bearing portion of a patient's body, and a catheter member having proximal and distal ends and at least one lumen extending-therebetween. The structural support is preferably configured to fit within a resected cavity in a patient's bone, and more particularly in a patient's spine. At least one anchoring element is disposed proximate to the distal end of the catheter and is adapted to fit within the internal space in the structural support so as to anchor the distal end of the catheter therein. The system also includes a radiation source disposable within the internal space through the at least one lumen in the catheter for delivering radiation to the tissue surrounding the interstitial space.

The system can be adapted to control the distribution of radiation to tissue surrounding the interstitial space. In one embodiment, a shield can be formed on a portion of at least one of the structural support and the anchoring element for shielding radiation sensitive tissue from a portion of the radiation. Alternatively, or in addition, a portion of the structural support adapted to be positioned adjacent to a patient's spine or other vital organs and structures can be formed from a radio-opaque material adapted to shield the patient's spinal cord from radiation. In yet another embodiment, the radiation source can be configured to provide an asymmetric radiation dose within the tissue surrounding the interstitial space so that radiation sensitive tissue surrounding the interstitial space receives a lesser dose. In other aspects, the anchoring element can be an outer expandable member, and the system can include an inner expandable member disposable within the outer expandable member and effective to removably receive the radiation source. Preferably, the outer expandable member is adapted to be positioned substantially adjacent to tissue surrounding the interstitial space when expanded, and the inner expandable member is effective to position the radiation source at a predetermined distance apart from the outer expandable member to provide a minimum absorbed dose for delivering radiation to tissue adjacent the outer expandable member. In another embodiment, at least one of the outer expandable member and the inner expandable member can be partially coated with a radio-opaque material effective to shield radiation sensitive tissue from a portion of the radiation source. Alternatively, or in addition, a shield effective to shield radiation sensitive tissue from a portion of the radiation source can be disposed between the outer expandable member and the inner expandable member.

In another embodiment of the present invention, a brachytherapy system for delivering radioactive emissions to an interstitial space in a resected vertebral body is provided. The system includes a cage member adapted to fit within an interstitial space in a resected vertebral body and having an internal space, a catheter body having proximal and distal ends, and a first expandable balloon member disposed adjacent the distal end of the catheter body and defining an inner spatial volume having a radiation source disposed therein. The first expandable balloon member is adapted to be disposed within the internal space in the cage member.

In other aspects of the present invention, a method for treating spinal metastases is provided. The method includes the steps of surgically resecting a vertebral body to create an interstitial space, providing an interstitial brachytherapy apparatus for delivering radioactive emissions, intraoperatively placing the interstitial brachytherapy apparatus into the interstitial space, providing a controlled dose of radiation to tissue surrounding the apparatus, and removing the interstitial brachytherapy apparatus. The apparatus preferably includes a catheter member having proximal and distal ends and at least one lumen, at least one anchoring element disposed proximate to the distal end of the catheter and adapted to anchor the distal end of the catheter within the interstitial space, and a radiation source disposable within the internal space through the at least one lumen in the catheter for delivering radiation to the tissue surrounding the interstitial space. The step of surgically resecting a vertebral body can further include the step of providing a structural support adapted to fit within the interstitial space, and positioning the structural support in the interstitial space, wherein the interstitial brachytherapy apparatus is positioned in an internal space within the structural support. The radiation source is preferably placed into the interstitial brachytherapy apparatus after placement of the apparatus into the internal space in the structural support, and is preferably removed from the internal space in the structural support before removal of the apparatus.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

The present invention generally provides a radiotherapy system, and preferably a brachytherapy system, for delivering radiation to tissue and/or bone surrounding an interstitial space. While the system can be used for a variety of purposes, the system is preferably used to treat spinal metastases. In general, the system 10 (FIG. 1) includes a catheter member 12 having a proximal end 14, a distal end 16, and an inner lumen 18 (FIG. 3) extending therethrough, and a structural support 20 adapted to fit within an interstitial space 22 in load bearing portion of a patient's body and having an internal space 24 for removably receiving the distal end 16 of the catheter member 12. At least one anchoring element 46 can be disposed proximate to the distal end 16 of the catheter 12. The anchoring element 46 is preferably adapted to fit within the internal space 24 in the structural support 20 so as to anchor the distal end 16 of the catheter 12 therein. The system 10 further includes a radiation source (not shown) disposable within the internal space 24 of the structural support 20 through the lumen 18 in the catheter 12 for delivering radiation to tissue surrounding the interstitial space 22.

Figure 2:
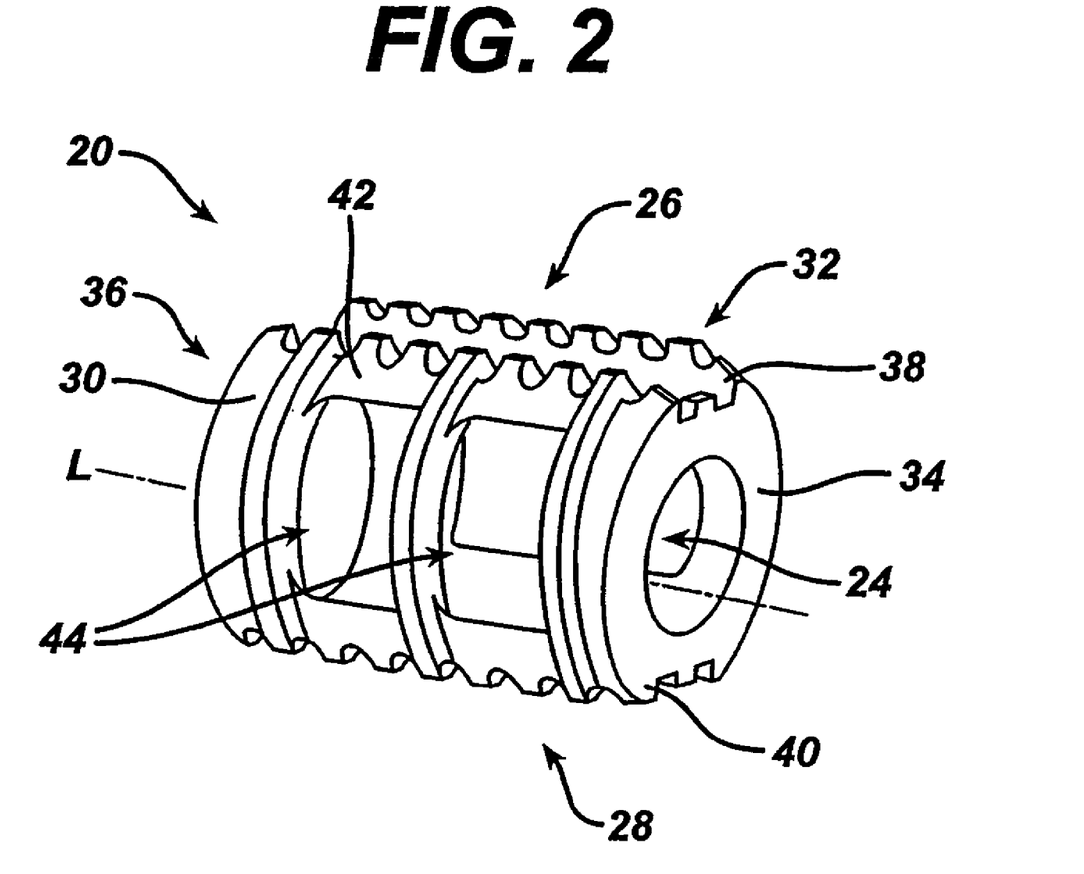
FIG. 2 is a perspective view illustration of one embodiment of a structural support member for use with the system of the present invention.

The structural support 20 used with the system 10 of the present invention can have a variety of configurations, but is preferably a cage-like member adapted to fit within a resected vertebrae 50 and to receive a load bearing portion of the vertebrae 50. The support 20 can have any shape and size, but should include an internal space 24 formed therein for receiving the distal end 16 of the catheter member 12. In an exemplary embodiment, the structural support 20 is a spinal fusion cage. FIG. 2 illustrates one example of a suitable structural support 20 for use with the system 10 of the present invention. The illustrated support is the BP® Cage manufactured by Sulzer Spine-Tech and described in U.S. Pat. Nos. 5,015,247, 5,484,437 and 5,741,253. Other suitable supports for use with the system of the present invention include, for example, the Ray TFC® manufactured by Surgical Dynamics Inc. and described in U.S. Pat. Nos. 5,015,247, 5,484,437, and 5,741,253, and the Infuse® Bone Graft and the LT-CAGE® manufactured by Medtronic Sofamor Danek. A person having ordinary skill in the art will appreciate that a variety of structural supports can be used, and that the support can include a variety of features not shown or described herein.

As shown in FIG. 2, the BP Cage 20 has a generally elongate, cylindrical shape and includes an internal space 24 formed therein. The cage 20 includes superior and inferior surfaces 26, 28, first and second transverse sides 30, 32 extending between the superior and inferior surfaces 26, 28, and proximal and distal ends 34, 36. An inner lumen, which forms the internal space 24, extends between the proximal end 34 and the distal end 36 of the cage 20 along a longitudinal axis L. The proximal end 34 of the cage 20 is open for receiving the distal end 16 of the catheter 12. The distal end 36 is also open, but can be solid to prevent over-insertion of the catheter 20 and/or to shield radiation-sensitive tissue from radiation, as will be discussed in more detail below. The cage 20 further includes one or more openings 44 extending through each of the transverse sides 30, 32 for receiving bone-growth promoting materials. The openings 44 can also be strategically placed to control the direction of radiation delivered to the tissue surrounding the interstitial space, as will also be discussed in more detail below. The cage 20 can also be adapted to mate with an insertion tool (not shown). For example, the superior and inferior surfaces 26, 28 of the cage 20 can include one or more grooves 38, 40 formed therein for receiving an insertion tool, and threads 42 disposed there around for facilitating insertion of the cage 20 into an interstitial space. In use, the cage 20 can be grasped by an insertion tool and rotated to thread the cage 20 into an interstitial space. A person having ordinary skill in the art will appreciate that a variety of insertion tools and mating techniques can be used to position the cage in a resected cavity.

Figure 1:
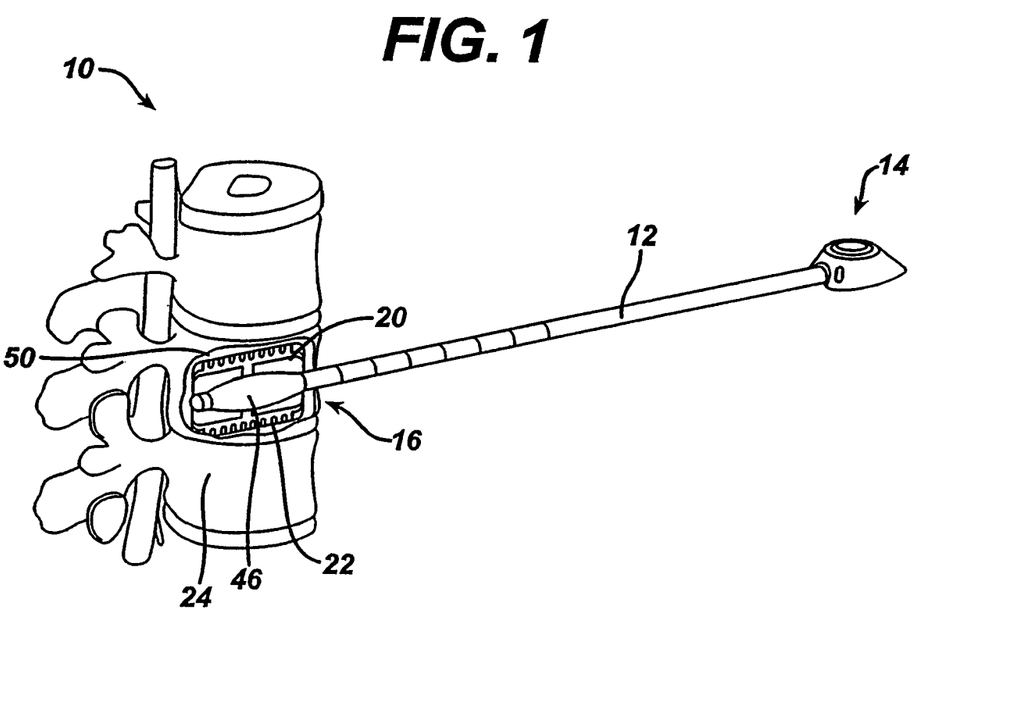
FIG. 1 is perspective view illustration of a brachytherapy system for treating spinal metastases in a resected vertebrae.

The catheter member 12 used with the system 10 of FIG. 1 can also have a variety of configurations, but is preferably a brachytherapy apparatus used to deliver radiation to tissue surrounding a resected cavity. A person having ordinary skill in the art will appreciate that virtually any brachytherapy apparatus can be used with the system 10 of the present invention. By way of non-limiting example, a suitable brachytherapy apparatus for use with the system of the present invention is disclosed in U.S. Pat. No. 6,413,204, issued Jul. 2, 2002, and entitled "Interstitial Brachytherapy Apparatus and Method for the Treatment of Proliferative Tissue Diseases," which is hereby incorporated by reference herein.

Figure 3:
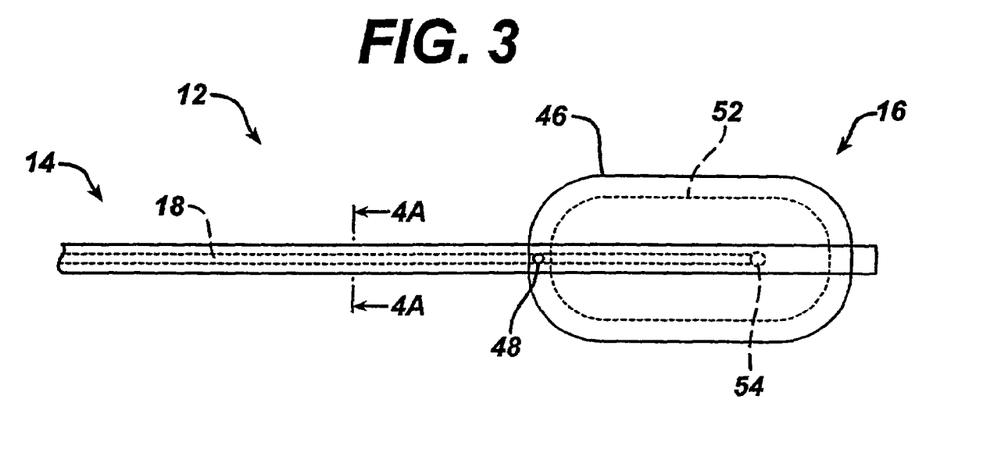
FIG. 3 is a diagram illustrating one embodiment of a catheter member for use with the system of the present invention.

FIG. 3 illustrates an exemplary embodiment of a catheter member 12 for use with the system 10 of the present invention. As shown, the catheter member 12 includes a proximal end 14, a distal end 16, and at least one inner lumen 18 extending therebetween. The distal end 16 includes an anchoring element 46 disposed thereon for anchoring the distal end 16 of the catheter 12 within the internal space 24 of the cage member 20. At least one lumen 18 of the catheter 12 preferably includes a port 48 in communication with the anchoring element 46 for expanding the anchoring element 46. The anchoring element 46 can have virtually any configuration, but is preferably an expandable balloon member, as shown in FIG. 3, that is primarily sealed around the port 48 on the distal end 16 of the catheter member 12. In use, the expandable member 46 is movable between a deflated position to allow insertion of the distal end 16 of the catheter 12 into the internal space 24 in the support member 20, and an inflated position, as shown, wherein air or fluid is delivered through the lumen 18 and the port 48 in the catheter 12 to inflate the expandable member 46 and thereby anchor the distal end 16 of the catheter member 12 in the internal space 24 of the support 20. The anchoring element 46 can have any shape and size, but preferably has a predetermined shape in its expanded form, as shown in FIG. 3, such that, when inflated, the anchoring element is adapted to securely fit within the internal space 24 of the structural support 20 to positively locate the distal end 16 of the catheter 12 with respect to the cage 20 and with the target tissue to be dosed with radiation. While the size of the anchoring element 46 can be predetermined, the size can be selectable during treatment by inflating the anchoring element 46 to a desired level. In an alternative embodiment (not shown), the anchoring element 46 can be an expandable cage member, and the catheter 12 can optionally include a control lever or similar mechanism for moving the expandable cage member between a contracted position and an expanded position. A person having ordinary skill in the art will appreciate that a variety of anchoring elements can be used with the present invention.

Figure 4A:
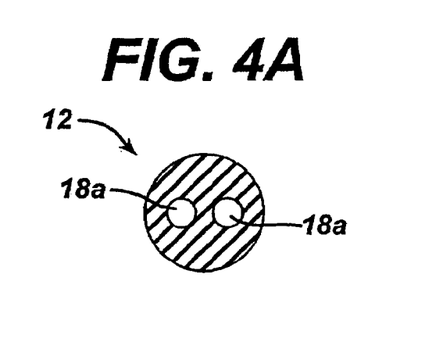
FIG. 4A is a cross-sectional view of the catheter member shown in FIG. 3 taken across line A-A.

The catheter 12 can also optionally include a second, inner expandable member 52 disposed within the first, outer expandable member 46. The inner expandable member 52 is also preferably an expandable balloon member and is effective to receive a radiation source. The inner expandable member 52 can have any shape and size, but is preferably adapted to fit within the outer expandable member 46 and, when inflated, to be spaced a predetermined distance apart from the outer expandable member 46. In use, the inner expandable member 52 is movable between a deflated position, in which the expandable member 52 is disposed adjacent the distal end of the catheter 16, and an inflated position, in which the inner expandable member 52 is disposed within, but spaced apart from, the outer expandable member 46. A second lumen 18b, shown in FIG. 4A, and a second port 54 are provided on the catheter 12 for communicating with the inner expandable member 52.

With no limitation intended, the inner and outer expandable members 46, 52 can be formed from a polymeric film wall, which may comprise a biocompatible, radiation resistant polymer. Suitable polymers include, for example, silastic rubbers, polyurethanes, polyethylene, polypropylene, polyester, and PVC.

The system 10 of the present invention is adapted to control the distribution of radiation to tissue surrounding the interstitial space. One advantage to controlling the distribution of radiation to tissue surrounding the interstitial space is that a minimum prescribed dose can be delivered to the tissue in the target treatment region without over-exposing radiation-sensitive tissue, which can cause healthy tissue necrosis.

In one embodiment, the structural support 20 can be adapted to allow radiation from a source within the cage to pass only to a desired region of tissue. For example, where the system 10 is used to treat a spinal metastases, the system 10 can be configured to provide less radiation in the direction of the spinal cord. By way of non-limiting example, the support 20 can be formed from a radio-opaque material and can include one or more radio-lucent regions for allowing radiation to be transmitted therethrough. Alternatively, the support 20 can be formed from a radio-lucent material and portions of the support can be coated with a radio-opaque shield effective to shield a desired region of tissue from radiation. The entire support 20 can also optionally be radio-lucent. Preferably, the distal end 36 of the support is radio-opaque to prevent radiation from coming into contact with a patient's spinal cord. In another embodiment, the support can be formed from a radio-opaque material and can include one or more openings, similar to the openings 44 illustrated in FIG. 2, that are effective to allow radiation to be delivered to a region of tissue positioned proximate to the openings.

In another embodiment, the anchoring element 46 and/or the inner expandable member 52 can be adapted to control the distribution of radiation to the tissue surrounding the interstitial space. For example, the inner expandable member 52 can be effective to receive a radiation source and to position the radiation source a predetermined distance apart from the outer expandable member 46, thereby providing a minimum absorbed dose for delivering radiation to tissue adjacent the outer expandable member 46. This configuration is described in more detail in U.S. Pat. No. 6,413,204, issued Jul. 2, 2002, and entitled "Interstitial Brachytherapy Apparatus and Method for Treatment of Proliferative Tissue Diseases," which is incorporated herein by reference. In general, the inner and outer expandable members have a volume that is configured to provide an absorbed dose within a predetermined range throughout a target tissue.

Figure 4B:
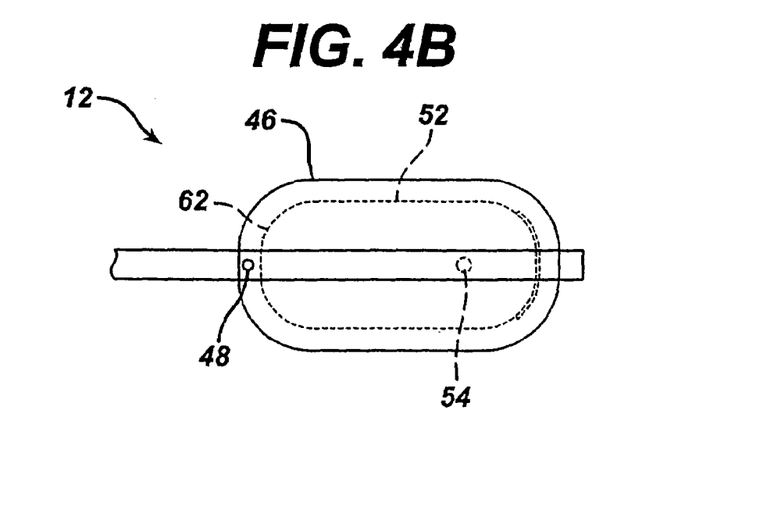
FIG. 4B is a diagram illustrating another embodiment of a catheter member for use with the system of the present invention having a radio-opaque coating disposed thereon for shielding radiation sensitive tissue.

In another embodiment, at least one of the anchoring element 46 and/or the inner expandable member 52 can be partially coated with a radio-opaque material effective to shield radiation sensitive tissue from a portion of the radiation source. By way of non-limiting example, FIG. 4B illustrates a radio-opaque material 62 coated onto a distal portion of the surface of the inner expandable member 52. The coating 62 can be strategically positioned to shield radiation sensitive tissue, and/or to provide an asymmetric isodose curve as described in U.S. patent application Ser. No. 09/464,727, filed on Dec. 16, 1999, and entitled "Asymmetric Radiation Dosing Apparatus and Method," which is incorporated herein by reference.

Radio-opaque materials suitable for coating onto an expandable surface include, for example, barium, tungsten, bismuth, tantalum, and tin. As an alternative to coating the inner and/or outer expandable members 46, 52 with a radio-opaque material, a radiation-blocking or absorbing shield (not shown) can be positioned between the anchoring element 46 and the inner expandable member 52, or within the inner expandable member 52 to produce a desired isodose curve. A person having ordinary skill in the art will appreciate that other configurations may be employed to achieve the desired isodose curves and/or shielding of radiation sensitive tissue.

Figure 5:
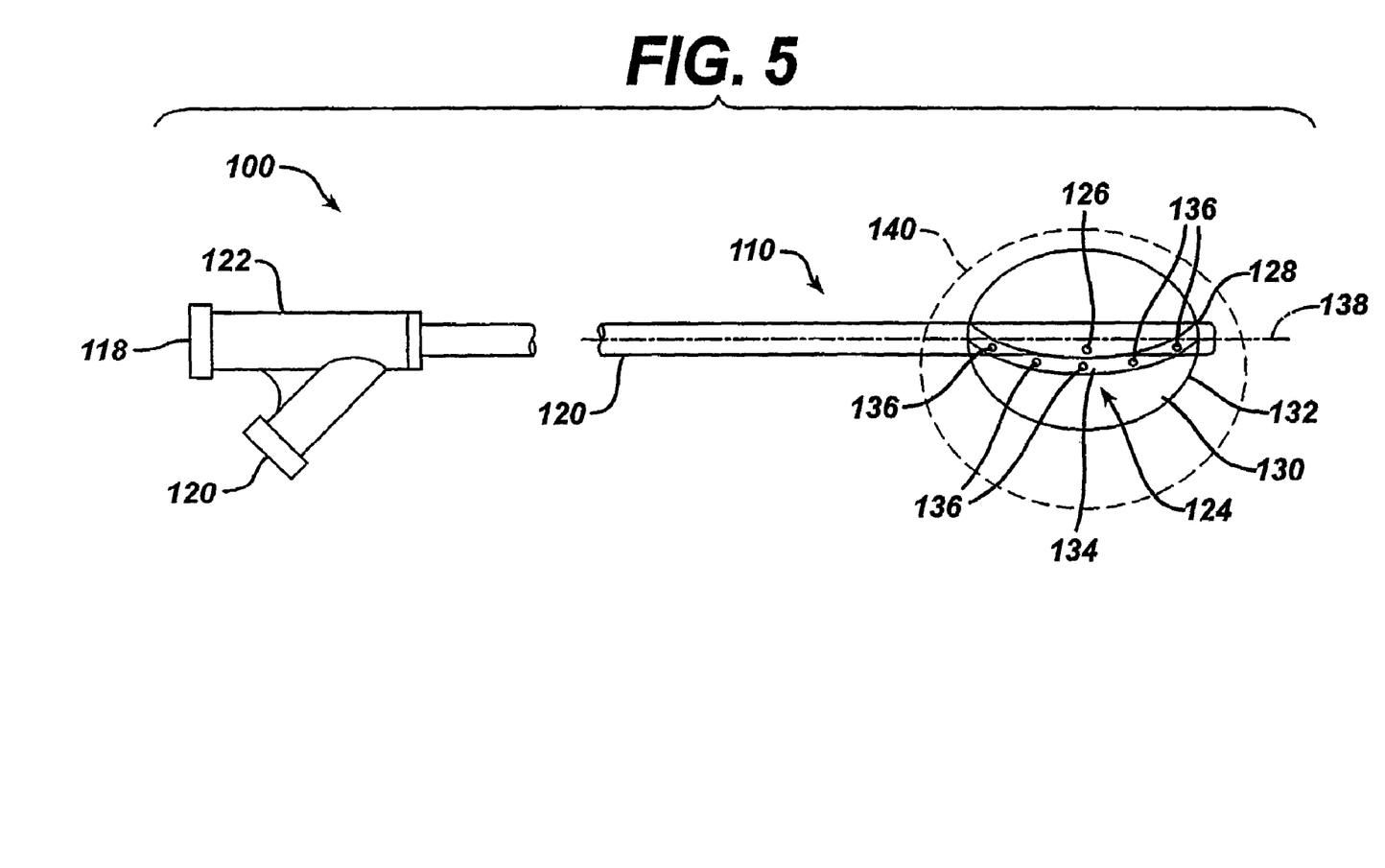
FIG. 5 is a side view of an interstitial brachytherapy apparatus for delivering asymmetric radioactive doses to body tissue.

In yet another embodiment, the radiation source itself can be configured to provide radiation to a desired region of tissue surrounding the interstitial space. By way of non-limiting example, FIG. 5 illustrates system 100 having a catheter 110 including first and second lumens (not shown) extending from first and second proximal ports 118, 120 in a molded hub 122. The first lumen is effective to carry a radioactive source 124 and the second lumen communicates with inflation port 126 formed through the side wall of the catheter member 110. The distal end 128 of the catheter 110 includes an outer spatial volume 130 defined by an outer polymeric film barrier 132 that is appropriately spaced from the radioactive source 124. The outer volume 130 encompasses inflation port 126. The radiation source 124 comprises a wire 134 having one or more solid radioactive particles 136 located thereon. The radioactive source 124 can either be preloaded into the catheter 110 at the time of manufacture, or loaded into the device after it has been implanted into the space formerly occupied by the excised tumor. If loaded after implantation, the solid radiation emitting material 136 can be inserted through the first lumen on a wire 134, for example, using an afterloader (not shown). Radiation source 124 has an asymmetric configuration with respect to a longitudinal axis 138 of the instrument 110. That is, radiation source 124 is shaped so as to result in an isodose profile 140 that varies radially about the longitudinal axis 138. More simply, the isodose profile 140 of FIG. 5 has a shorter radius from the longitudinal axis 138 on the top side of the instrument 110 as shown in FIG. 5 than on the bottom side. The asymmetrically shaped isodose curve 140 may be created by providing a plurality of solid radioactive particles 136 on a curved wire 134 in a spaced apart relationship. This configuration will result in certain of the solid radioactive particles 136 being farther from the longitudinal axis 138 of the instrument 110 than others, and will result in the illustrated asymmetric isodose profile 140. One way to provide the illustrated radioactive source 124 configuration is to form wire 134 from a solid or tubular shape memory alloy such as nickel-titanium alloys known in the art to have such properties. Wire 134 can then be preformed to the desired shape, can be compressed into a substantially straight configuration to pass through the first lumen, and will resume its desired shape once inside volume 130 where wire 134 will be free from steric constraints imposed inside the first lumen. The resulting asymmetric isodose curve 140 can be further tailored by using solid radioactive particles 136 having differing specific activities to achieve the desired dosing. Such a configuration is also described in U.S. patent application Ser. No. 09/464,727, filed on Dec. 16, 1999, and entitled "Asymmetric Radiation Dosing Apparatus and Method."

In use, the support member 20 is preferably positioned within a resected cavity in a patient's body, preferably within an interstitial space created in a resected vertebrae 50, as shown in FIG. 1. The distal end 16 of the catheter member 12 is then anchored in the internal space 24 in the support member 20 by inflating the anchoring element 46. The anchoring element 46 can be inflated with air or other fluids, such as saline or a radiation absorbing fluid such as a contrast media used in angiography. The catheter 12 can be pre-loaded with a radioactive source, or alternatively the radioactive source can be inserted into the catheter 12 via lumen 18. The radioactive source dwells in the distal end 16 of the catheter 12, preferably in the inner expandable member 52, until the prescribed dose of radiotherapy is delivered, or the radioactive source can be inserted for prescribed amounts of time on a daily or other scheduled basis until the prescribed dosage has been achieved. The radioactive source is then retrieved and the catheter 12 is removed. The radiation treatment may end upon removal of the brachytherapy apparatus 12, or the brachytherapy may be supplemented by further doses of radiation supplied externally.

Suitable radiation sources for use with the system of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel. One radioactive material useful in the invention is Iotrex™, a sterile single use, non-pyrogenic solution containing sodium 3-($^{125}$I)iodo-4-hydroxybenzenesulfonate ($^{125}$I-HBS), available from Proxima Therapeutics, Inc. of Alpharetta, Ga. Radioactive micro spheres of the type available from the 3M Company of St. Paul, Minn., may also be used. This radioactive source can either be preloaded into the catheter at the time of manufacture or loaded into the device after it has been implanted into the space formerly occupied by the excised tumor with one or more solid radioactive micro spheres inserted through the catheter on a wire, for example, using an afterloader (not shown).

A method according to the invention for treating spinal metastases and other malignancies begins by surgically resecting a vertebral body to create an interstitial space. Following tumor resection, but prior to closing the surgical site, the surgeon intra-operatively places an interstitial brachytherapy apparatus, having a catheter member with at least one anchoring element as described above, into the interstitial space in the resected cavity. A radiation source is then positioned within the internal space in the anchoring element through at least one lumen in the catheter for delivering a controlled dose of radiation to the tissue surrounding the interstitial space. The brachytherapy apparatus is then removed. In a further embodiment, the step of surgically resecting a vertebral body can further include the step of providing a structural support adapted to fit within the interstitial space, and positioning the structural support in the interstitial space. In this embodiment, the interstitial brachytherapy apparatus is positioned in an internal space within the structural support. The radiation source is preferably placed into the interstitial brachytherapy apparatus after placement of the apparatus into the internal space in the structural support, and is removed from the internal space in the structural support before removal of the apparatus.

A person having ordinary skill in the art will appreciate that the brachytherapy system of the present invention can have virtually any configuration, and the embodiments illustrated and described herein are intended merely as exemplary embodiments and should not be construed to limit the present invention. Moreover, it will be understood that the foregoing is only illustrative of the principles of the invention, and that various modifications can be made by those skilled in the art without departing from the scope and spirit of the invention. All references cited herein are expressly incorporated by reference in their entirety.

The invention claimed is:

1. A system for treating metastases in a load bearing portion of a patient's body, comprising:
   a structural support adapted to fit in an interstitial space in a load bearing portion of a patient's body and to structurally stabilize the load bearing portion, the structural support defining an internal space;
   a radiation source independently positionable within the internal space for delivering radiation to tissue surrounding the interstitial space.

2. The system of claim 1, further comprising a shield, the shield being adapted to shield radiation sensitive tissue from a portion of the radiation.

3. The system of claim 1, wherein the structural support is configured to fit within a cavity in a patient's bone.

4. The system of claim 1, wherein the structural support is configured to fit within a cavity in a patient's spine.

5. The system of claim 4, wherein a portion of the structural support adapted to be positioned adjacent a patient's spine is formed from a radio-opaque material adapted to shield the patient's spinal cord from radiation.

6. The system of claim 1, wherein the radiation source is configured to provide an asymmetric radiation dose within the tissue surrounding the interstitial space so that radiation sensitive tissue surrounding the interstitial space receives a lesser dose.

7. The system of claim 1, wherein the structural support and the radiation source are adapted so that the radiation source is positioned at a predetermined distance apart from tissue surrounding the cavity so as to provide a prescribed absorbed dose of radiation to the surrounding tissue to a predetermined depth.

8. A method for treating metastases in a load bearing portion of a patient's body, comprising:
   placing a structural support within an interstitial space in the load bearing portion of the patient's body to provide structural support therein;
   placing a radiation source independently within the structural support; and
   providing a controlled dose of radiation to tissue surrounding the structural support.

9. The method of claim 8, further comprising surgically resecting a vertebral body to at least partially create an interstitial space.

10. The method of claim 8, wherein a radiation shield is provided, the shield being adapted to shield radiation sensitive tissue from a portion of the radiation.

11. The method of claim 10, wherein a portion of the structural support is formed from a radio-opaque material adapted to shield the patient's spinal cord from radiation.

12. The method of claim 8, wherein the radiation source is configured to provide an asymmetric radiation dose within the tissue surrounding the interstitial space so that radiation sensitive tissue surrounding the interstitial space receives a lesser dose.

13. The method of claim 8, wherein the radiation source is positioned so as to provide a prescribed absorbed dose of radiation to tissue surrounding the cavity to a predetermined depth.

14. The method of claim 8, wherein the radiation source comprises at least one solid radiation source disposed on at least one elongate member.

15. The method of claim 8, wherein a plurality of solid radiation sources are disposed in a spaced apart relationship on a single elongate member.

* * * * *